US 9,804,124 B2

(12) United States Patent
Sabouroux

(10) Patent No.: US 9,804,124 B2
(45) Date of Patent: Oct. 31, 2017

(54) UNIVERSAL SAMPLE HOLDER FOR MEASURING THE ELECTROMAGNETIC PROPERTIES OF A DIELECTRIC AND/OR MAGNETIC MATERIAL

(75) Inventor: Pierre Sabouroux, Plan de Cuques (FR)

(73) Assignee: UNIVERSITE D'AIX-MARSEILLE, Marseilles (FR)

( * ) Notice: Subject to any disclaimer, the term of this patent is extended or adjusted under 35 U.S.C. 154(b) by 562 days.

(21) Appl. No.: 14/119,646

(22) PCT Filed: May 31, 2012

(86) PCT No.: PCT/FR2012/051219
§ 371 (c)(1),
(2), (4) Date: Feb. 19, 2014

(87) PCT Pub. No.: WO2012/164229
PCT Pub. Date: Dec. 6, 2012

(65) Prior Publication Data
US 2014/0174210 A1 Jun. 26, 2014

(30) Foreign Application Priority Data
Jun. 1, 2011 (FR) .................................. 11 01697

(51) Int. Cl.
*G01N 1/00* (2006.01)
*G01N 27/72* (2006.01)
*G01R 27/26* (2006.01)

(52) U.S. Cl.
CPC ............... *G01N 27/72* (2013.01); *G01N 1/00* (2013.01); *G01R 27/2664* (2013.01)

(58) Field of Classification Search
CPC ....................................................... G01N 1/00
See application file for complete search history.

(56) References Cited

U.S. PATENT DOCUMENTS 2,889,736 A * 6/1959 Borg ............................... 356/70
4,147,062 A * 4/1979 Jaeger .................. G01N 1/2035
73/863.83
(Continued)

FOREIGN PATENT DOCUMENTS

FR 2619223 A1 2/1989
FR 2862758 A1 5/2005

OTHER PUBLICATIONS

International Search Report for corresponding application PCT/FR2012/051219 dated May 31, 2012; dated Aug. 31, 2013.
(Continued)

*Primary Examiner* — Robert R Raevis
(74) *Attorney, Agent, or Firm* — Cantor Colburn LLP

(57) ABSTRACT

The invention relates to the technical field of measuring electric and magnetic properties, and specifically relates to a sample holder (1) to be connected to a device (2) for supporting a sample holder in order to measure the dielectric and/or magnetic properties of a sample (3), said supporting device (2) comprising: first and second connectors (4, 5) suitable for allowing an electromagnetic wave to pass therethrough, and for being connected to a means (6) for transmitting the electromagnetic wave and to a means (7) for circulating the electromagnetic wave after passing through the supporting device (2) and the sample holder (1), respectively, which is suitable for transmitting all or part of the electromagnetic wave from the first connector (4) to the second connector (5) according to a reference axis (x) and for being removably arranged therebetween, the sample holder (1) comprising an outer tubular body (11) that is coaxial to said reference axis (x), and a cavity (8) in which the sample (3) is to be housed, the sample holder further comprising sidewalls (9) positioned transversely to the ref-
(Continued)

erence axis (x) on either side of the cavity (8), which said walls thus laterally seal.

14 Claims, 4 Drawing Sheets

(56) References Cited

U.S. PATENT DOCUMENTS

| | | | | |
|---|---|---|---|---|
| 5,585,576 | A | * | 12/1996 | Jaeger ................. G01N 1/10 73/863.54 |
| 5,759,797 | A | * | 6/1998 | Horigane et al. ............... 435/29 |
| 2014/0158911 | A1 | * | 6/2014 | Sahiri et al. ............... 250/458.1 |

OTHER PUBLICATIONS

P. Sabouroux, "Epsimu, a tool for dielectric properties measurement of porous media: Application in wet granular materials characterization" Progress in Electromagnetics Research B., No. 29, Mar. 30, 2011, pp. 191-207.

Doudou Ba, "EpsiMu, A Toolkit for Permittivity and Permeability Measurement in Microwave Domain at Real ime of All Materials; Applications to Solid and Semisolid Materials", Microwave and Optical Technologies Letters, vol. 52, No. 12 Dec. 2010, pp. 2643-2648, XP002667848.

* cited by examiner

UNIVERSAL SAMPLE HOLDER FOR MEASURING THE ELECTROMAGNETIC PROPERTIES OF A DIELECTRIC AND/OR MAGNETIC MATERIAL

TECHNICAL FIELD OF THE INVENTION

The technical field of the invention is that of measurements of electrical and magnetic characteristics and more particularly that of measurements of electromagnetic characteristics of a dielectric and/or magnetic material. The subject of the invention is therefore a sample holder to be linked to a support device of a sample holder for measurements of dielectric and/or magnetic characteristics of a sample and an associated support device.

PRIOR ART

The problem area posed by appliances for measuring electromagnetic characteristics of a dielectric or magnetic material has already spurred several solutions, in particular that consisting in placing such a dielectric or magnetic material in a measurement cell, in particular a coaxial measurement cell, said cell being linked to a network analyzer.

In this regard, patent of invention FR 2619223 A1, which describes a method and a device for estimating the electromagnetic characteristics of a dielectric and/or magnetic material, is known. More precisely, the document discloses a support device of a sample holder for measurements of dielectric and/or magnetic characteristics of a sample, said support device comprising: a first and a second connector suitable for allowing an electromagnetic wave to pass therethrough and comprising means of guidance of the wave along a reference axis, a first connection means situated at a first end of the first connector for connecting it to a means for transmitting an electromagnetic wave and applying it in the means of guidance of the first connector, a second connection means situated at a first end of the second connector for receiving the electromagnetic wave originating from the means of guidance of the second connector and making it circulate toward processing means, the sample holder being able to transmit all or part of the electromagnetic wave from the first to the second connector along a reference axis and to be disposed therebetween in a mutually removable manner. Furthermore, the sample holder encloses a cavity where the sample is housed. More precisely, the sample holder comprises a tubular external body surrounding, coaxially with said reference axis, said cavity where the sample is housed.

The drawback of such a device is in particular that of requiring a cavity for an annular member of uniform thickness fashioned from said dielectric and/or magnetic material. Indeed this annular member is such that, when it is disposed in said cavity, its exterior and interior peripheries are respectively in tight frictional contact with the surface of the cavity. Consequently, such a device exhibits drawbacks of implementation during the measurements performed since it requires a dismantling of the sample holder and a step of putting said material in place, resulting in a loss of time and of precision between two successive measurements.

Moreover, though such a device is able to measure electromagnetic characteristics of solid materials, it nonetheless exhibits, in particular for materials of liquid or gel types, limitations such as the packaging of the materials in the cavity, or indeed the flowing of the material in the case where the measurements are performed on a material requiring a dynamic flow, or continuous measurements in real time.

Furthermore, another shortcoming is related to the difficulty of rendering the device sterile for measurements of biological environments.

Moreover, certain measurement systems known from the prior art for measurements of liquids are either not very precise, or usable over a narrow frequency band, this being the case for capacitive or resonator type devices, or else limited to a single parameter, for example permittivity, this being the case in particular for slides implementing techniques based on end-effect coaxial probes also called "open ended coaxial cell".

DISCLOSURE OF THE INVENTION

The invention is aimed at remedying at least some of the drawbacks of the prior art, in particular the problems of dismantling a measurement cell so as to change the dielectric and/or magnetic sample material thereof and of packaging such a material with the aim of improving its implementation.

With this objective and according to a first aspect, it is envisaged, as a supplement to document FR 2619223 A1, that the cavity of the sample holder be bounded in a direction by lateral walls situated on either side of the cavity, transversely to the reference axis.

More precisely, the sample holder comprises lateral walls situated transversely to the reference axis, on either side of the cavity that they thus bound laterally. Stated otherwise, the cavity is thus delimited both:
  by a wall of the tubular external body surrounding, coaxially with said reference axis, said cavity; and
  by walls disposed transversely to the reference axis on either side of the cavity thus closing it laterally.

Such a sample holder exhibits numerous advantages. In particular, it exhibits the advantage of being able to be interchangeable. Indeed, the lateral walls disposed on the sample holder, transversely to the reference axis, and on either side of the cavity that they thus close laterally, guarantee the interchangeable character of said sample holder. It is then possible to change the samples without destroying them since the sample holder which contains the sample is changed along with the sample. Moreover, it is entirely possible to preserve samples without destroying them in sample holders, doing so in order to characterize said samples repeatedly if need be. Such a sample holder, insertable into the cell, is therefore interchangeable and reusable.

Another advantage is to be able to confine in a cavity of the sample holder, various types of substances, in particular all or some of solid, liquid, gaseous or grainy substances. Furthermore, the use of this sample holder makes it possible to manipulate the sample of substance without contact, the latter being packaged in the sample holder before the measurement operations, thereby making it possible to comply with cleanliness conditions in particular. In particular, but said sample holder can undergo pretreatments such as sterilization in the case where the materials to be characterized are sensitive to pollution from the environment such as for example biological materials.

Advantageously, said lateral walls are removable. This characteristic makes it possible in particular to be able to change the substance sample and/or to adapt the size of the cavity.

Moreover, according to a particular characteristic, the sample holder comprises:
- a central core;
- the tubular external body surrounding the central core, coaxially with the reference axis;
- means of leaktight assembly able to link, in a gas-tight and/or liquid-tight manner, the lateral walls to the central core and/or to the external body;
- the cavity being surrounded by the central core, the external body and the lateral walls. In the case where the central core and the external body are substantially circular, the cavity is substantially disk-shaped, its thickness being the distance between the lateral walls.

These characteristics allow the sample holder to be afforded a cavity in which a material can be packaged while complying with the conditions of leaktightness, cleanliness and optional sterility, this material being able to be either solid or liquid. Consequently, it is possible to manipulate a sample holder while preserving optimal packaging of the sample material in a sterile environment.

According to a specific characteristic, the sample holder comprises:
- means of entry and of exit of the sample allowing a flow of material in the cavity, in the case where the sample is made of pouring material. The expression "pouring material" is intended to connote a material in liquid or viscous form, for example fluids or gels. Such means allow measurements of electromagnetic characteristics of a dielectric and/or magnetic substance exhibiting and/or requiring a dynamic flow in order to be able to perform continuous measurements in real time while guaranteeing the interchangeability of the sample holder;

and/or

- means of measurement of intrinsic characteristics of the sample and/or means able to vary these intrinsic characteristics in the sample holder.

The expression "intrinsic characteristics" of the materials is intended to connote physical quantities that can be measured in an objective manner, these being all the mechanical, thermal, electrical, magnetic, optical properties.

For example, in the case where the intrinsic characteristic considered is the temperature, a means for measuring the temperature of the sample can be an electrical thermometer linked to a measurement probe comprising at least one resistor, and a means able to vary the temperature can be a resistor.

Advantageously, the lateral walls of the sample holder are made of dielectric material(s), in particular so as to be transparent to the propagation of electromagnetic waves, and/or the central core and the external body are made of electrically conducting material(s).

According to another particular characteristic, the central core exhibits along the reference axis a first end and a second end suitable for engaging by fastening the first and second connectors.

In an advantageous manner:
- the central core exhibits a central part and, laterally, a shaft extending along the reference axis on either side of the central part, the disk-shaped lateral walls being respectively received on the shaft, where they are clamped by first clamping means belonging to the means of leaktight assembly, and/or

- laterally the external body exhibits recesses where the lateral walls are received and clamped by second clamping means belonging to the means of leaktight assembly.

Moreover, the invention also relates to a support device of a sample holder for measurements of dielectric and/or magnetic characteristics of a sample, said support device comprising:
- a first connector and a second connector suitable for allowing an electromagnetic wave to pass therethrough and comprising means of guidance of the wave along a reference axis;
- a first connection means situated at a first end of the first connector for connecting it to a means for transmitting an electromagnetic wave and applying it in the means of guidance of the first connector;
- a second connection means situated at a first end of the second connector for receiving the electromagnetic wave originating from the means of guidance of the second connector and making it circulate toward processing means.

According to a particular aspect, said support device comprises a sample holder, which comprises all or some of the previously stated characteristics and, is disposed in a removable manner between the first and second connectors.

Such a support device offers numerous advantages. Indeed, in addition to the advantages already developed previously, related to the sample holder, such a support device of said sample holder for measurements of dielectric characteristics makes it possible to perform fast measurements. Indeed, through the ease of interchangeability of said sample holder, such a support makes it possible, by means of a single frequential measurement, to obtain results in quasi-real time.

Moreover, according to another characteristic, the first and second connectors each exhibit shoulders where the sample holder is housed and positioned.

Advantageously, the support device comprises third means for clamping the first connector on the second connector, away from the sample holder, the third means of clamping being in this manner fixed to the first and to the second connectors.

BRIEF DESCRIPTION OF THE FIGURES

Other characteristics and advantages of the invention will emerge on reading the description which follows, with reference to the appended figures, which illustrate.

For greater clarity, identical or similar elements are tagged by identical reference signs in all the figures.

DETAILED DESCRIPTION OF AN EMBODIMENT

Figure 1:
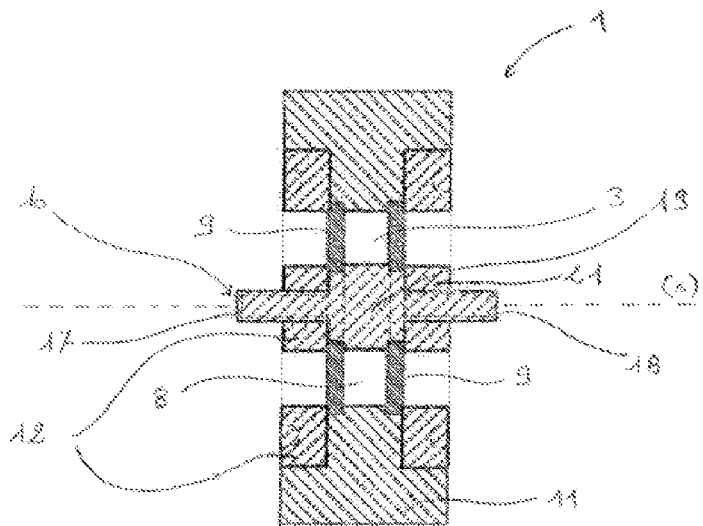
FIGS. 1 and 2, two diagrams of a sample holder according to one embodiment, representing respectively the sample holder assembled and in an exploded view.
Figure 2:
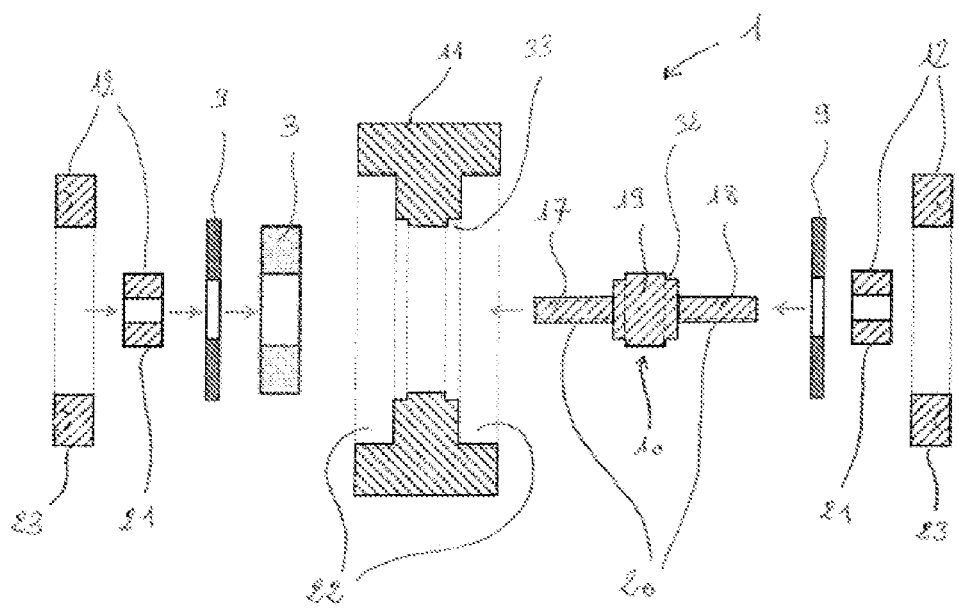

FIGS. 1 and 2 show two diagrams of a sample holder according to one embodiment, representing respectively the sample holder assembled and the sample holder in an exploded view.

Represented more particularly is a sample holder 1, enclosing a cavity 8 where a sample 3 is housed, said cavity 8 being closed by lateral walls 9 situated on either side of the cavity 8, transversely to a reference axis (x), the lateral walls being made of dielectric material(s).

It should be noted that in these figures and in this embodiment, the reference axis (x) constitutes an axis of revolution of the members represented.

More precisely, the sample holder 1 comprises:
a central core 10 made of electrically conducting material;
a tubular external body 11 surrounding the central core 10, coaxially with the reference axis (x), the external body 11 being made of electrically conducting material;
electrically conducting and leaktight material means of assembly 12 able to link, in a gas-tight and/or liquid-tight manner, the lateral walls 9 to the central core 10 and/or to the external body 11;
the cavity 8 being surrounded by the central core 10, the external body 11 and the lateral walls 9.

In different embodiments, the cavity 8 can also be surrounded by additional seals able to ensure additional leaktightness. Moreover, said cavity 8 exhibits in this example a circular cross section but can be of different shapes.

The walls used in this embodiment are made of dielectric material, and can more particularly be made of dielectric material such as for example Teflon or polyvinyl chloride (PVC) according to needs and chemical compatibilities with the material under test placed in the cavity 8.

Moreover, the central core 10 exhibits, along the reference axis (x), a first end and a second end 17, 18 suitable for engaging by fastening and/or screwing the first and second connectors 4, 5. Indeed, more precisely, the central core 10 exhibits a central part 19 and, laterally, a shaft 20 extending along the reference axis (x) on either side of the central part 19, the disk-shaped lateral walls 9 being respectively received on the shaft 20, where they are clamped by second clamping means 21 belonging to the means of leaktight assembly 12. In this embodiment, the first and second ends 17, 18 are the ends of the shaft 20 projecting laterally to the central part. Thus, the shaft 20 exhibits two functions here: one being to receive the second clamping means 21, the second being to engage by fastening in the first and second connectors 4, 5.

Moreover, laterally the external body 11 exhibits recesses 22 where the lateral walls 9 are received and clamped by first clamping means 23 belonging to the means of leaktight assembly 12.

The lateral walls 9, each disk-shaped, exhibit an interior diameter and an exterior diameter:
the interior diameter of the lateral walls 9 being slightly smaller than the exterior diameter of the central part 19 of the central core 10; and
the exterior diameter of the lateral walls 9 being slightly greater than the interior diameter of the external body 11;
so that the lateral walls 9 can close the cavity thus delimited by the central core 10, the external body 11 and the lateral walls 9. More precisely, the central part 19 of the central core 10 and external body 11 comprise respectively lateral shoulders 32, 33 receiving in abutment the lateral walls 9.

The second clamping means 21 exhibit an internal diameter able to be fixed by screwing on either side of the central core 10 on the shaft 20 extending along the reference axis (x) and an exterior diameter substantially equal to the exterior diameter of the central part 19 of the central core 10 ensuring the fixing of the lateral walls 9 in the lateral shoulders 32.

In a substantially equivalent manner, the first clamping means 23 exhibit on the one hand, an exterior diameter able to be fixed by screwing on either side of the central core 10 in the recesses 22 of the external body 11 extending along the reference axis (x) and, on the other hand, an interior diameter substantially equal to the interior diameter of the external body 11 ensuring the fixing of the lateral walls 9 in the lateral shoulders 33.

In this configuration, the lateral walls 9 are therefore removable with respect to the external body 11 and to the central core 10.

Such a sample holder 1 makes it possible to study the characteristics of materials of very diverse natures such as solid, granular, pulverulent, liquid or gel materials.

Figure 3:
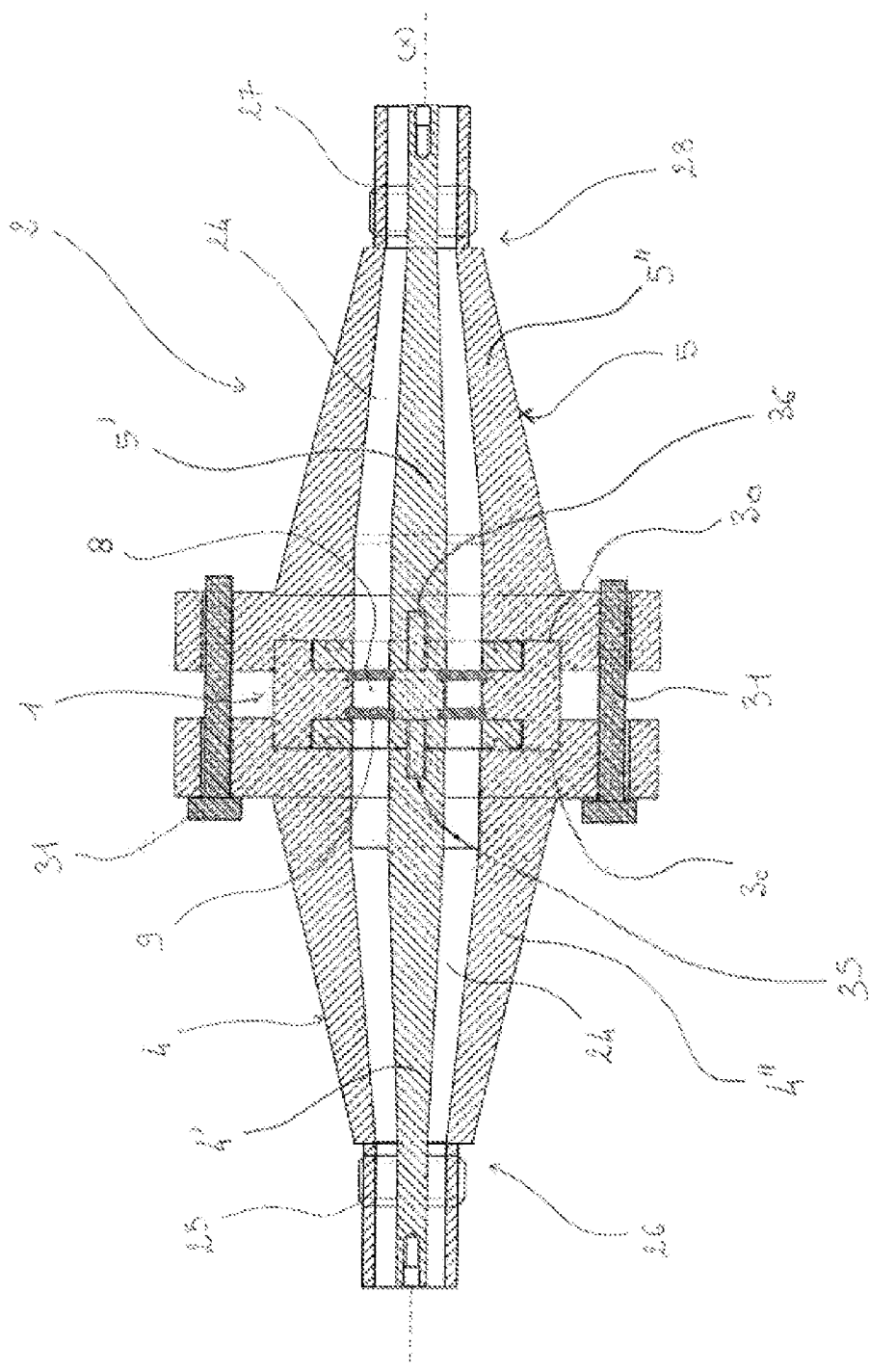
FIG. 3, a diagram of a support device according to one embodiment.

FIG. 3 shows a diagram of a support device according to one embodiment, comprising a sample holder 1 according to the embodiment illustrated in FIGS. 1 and 2.

Thus, represented is a support device 2 comprising:
a first connector and a second connector 4, 5 suitable for allowing an electromagnetic wave to pass therethrough and comprising means of guidance 24 of the wave along the reference axis (x);
a first connection means 25 situated at a first end 26 of the first connector 4 for connecting it to a means 6 for transmitting an electromagnetic wave and applying it in the means of guidance 24 of the first connector 4;
a second connection means 27 situated at a first end 28 of the second connector 5 for receiving the electromagnetic wave originating from the means of guidance 24 of the second connector 5 and making it circulate toward processing means 29.

Furthermore, the first and second connectors 4, 5 comprise:
a first core and a second core 4', 5' made of an electrically conducting substance;
a first tubular body and a second tubular body 4", 5", made of an electrically conducting substance, surrounding respectively the first and second cores 4', 5' so that the first and second cores 4', 5' and said connectors 4, 5 form a coaxial structure along the reference axis (x).

Thus, the means of guidance 24 of the electromagnetic wave is the coaxial structure itself, said electromagnetic wave being able to circulate in the space defined respectively between the first and second cores 4', 5' and between the first and second tubular bodies 4", 5".

Moreover, the first and second ends 17, 18 of the shaft 20 of the sample holder central core 10 are engaged by fastening respectively in the first and second connectors 4, 5, and more precisely in first and second cavities 35, 36 of the respective first and second cores 4', 5'. This configuration enables the sample holder 1 to be centered precisely in the support device 2. Stated otherwise, the cavity 8 of the sample holder 1 is centered with the means of guidance 24 and, a fortiori, with the lateral walls 9 so that the electromagnetic wave is able to circulate from the first connector 4 to the second connector 5 while passing through the cavity 8, which comprises the sample 3 of substance that is to be characterized.

Moreover, in this embodiment, the first and second connectors 4, 5 each exhibit shoulders 30 suitable for housing the sample holder 1, these said shoulders 30 being able therefore to also ensure good centering of the sample holder 1 between the first and second connectors 4, 5.

Also illustrated are third means of clamping 31 of the first connector 4 on the second connector 5, away from the sample holder 1. In this manner, the third means of clamping are fixed to the first and to the second connectors 4, 5. In particular in this embodiment, the first and second tubular bodies 4", 5" exhibit a substantially conical exterior surface whose base is widened so as to be able to receive said third clamping means 31.

Figure 4:
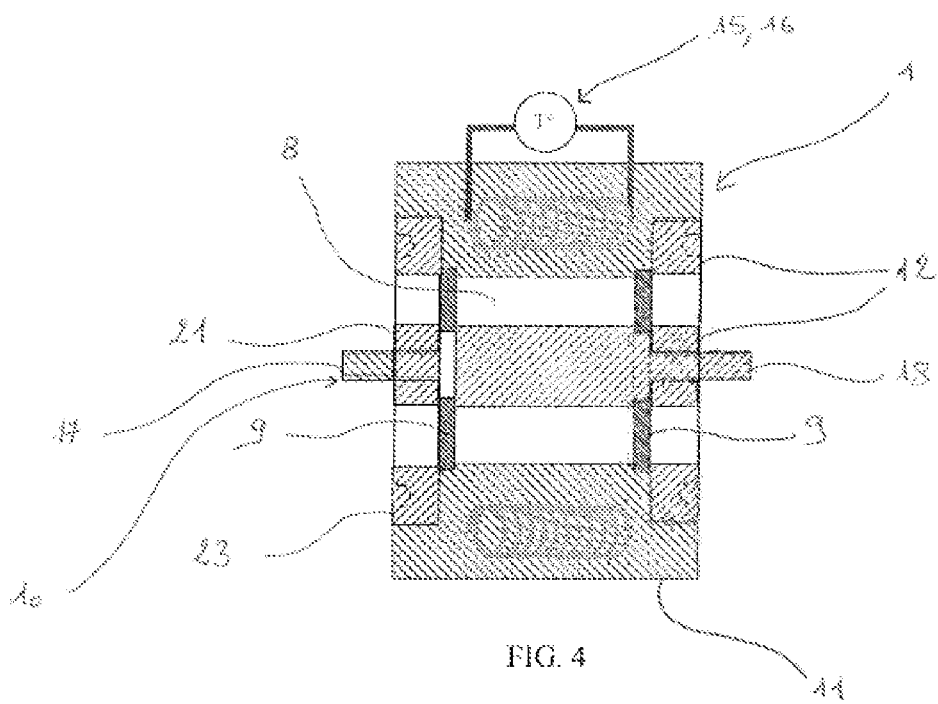
FIGS. 4 and 5, two diagrams of a sample holder according to two other different embodiments.
Figure 5:
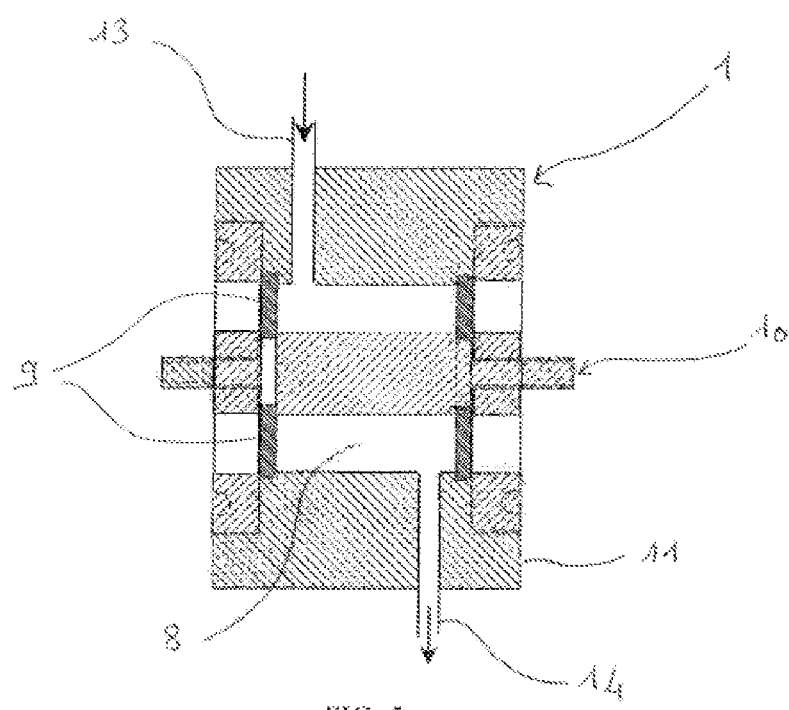

FIGS. 4 and 5 show two diagrams of a sample holder according to two other different embodiments.

Indeed, represented in FIG. 4 is a sample holder comprising, in addition to that illustrated in FIGS. 1 and 2, temperature measurement means 15, the temperature being an intrinsic characteristic of the sample 3, and means 16 able to vary this temperature in the sample holder 1, these means being able to be an electrically controlled resistor and a temperature probe linked to a thermometer.

Moreover, represented in FIG. 5 is a sample holder comprising, in addition to that illustrated in FIGS. 1 and 2, means of entry 13 and of exit 14 of the sample 3 allowing a flow of material in the cavity 8. This embodiment is optimal for studying the dielectric and/or magnetic characteristics of a sample of pouring material.

The expression "pouring material" is intended to connote a material in liquid or viscous form, for examples fluids or gels.

This configuration makes it possible in particular to study such a material exhibiting a dynamic flow, the direction of circulation of the fluid being demarcated here by way of indication by arrows.

This embodiment is thus particularly advantageous for performing continuous measurements over time and to view variations in real time of certain characteristics such as the amount of pollutant in an aqueous environment or else concentrations of liquids miscible in water.

It will have been noted that in all cases the cavity 8 is closed, thereby allowing the sample holder to be interchangeable, independently of its support device 2, and in particular of the first and second connectors 4, 5. In the variant of FIG. 5, the cavity 8 is actually closed, despite the means of entry 13 and of exit 14 of the sample, insofar as the walls 9 and the body 11 bound it fully over the whole of its periphery except for the entry 13 and exit 14 which merely constitute pointlike passages that can be closed and opened at will by a stopper and that therefore enable the sample holder to preserve its interchangeability.

Figure 6:
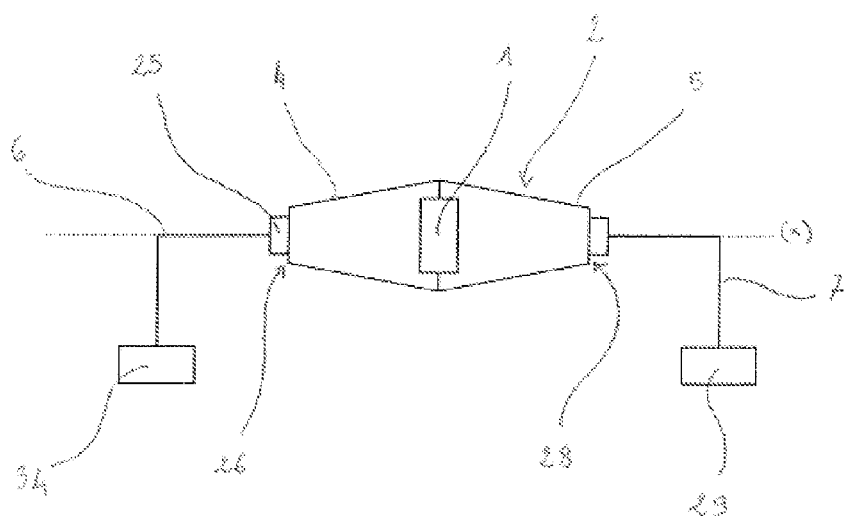
FIG. 6, a basic diagram of a measurement device comprising a support device and a sample holder according to one embodiment.

FIG. 6 shows a general basic diagram of a measurement device comprising a support device and a sample holder according to one embodiment.

Represented in particular in this figure is a general diagram of a device for measuring electromagnetic characteristics of a dielectric or magnetic material comprising sample holder 1 to linked to a support device 2 of the sample holder whose embodiment is detailed in FIG. 3, said support device 2 being connected:
- at the first end 26 of the first connector 4 to a means 6 for transmitting an electromagnetic wave from an emitter 34 and applying it in the means of guidance 24 of the first connector 4,
- to the first end 28 of the second connector 5 for receiving the electromagnetic wave originating from the means of guidance 24 of the second connector 5 and making it circulate toward processing means 29 by way of a means 7 for circulating the electromagnetic wave after its passage through the support device 2 and the sample holder 1.

The processing means 29 in the embodiment described here is a vector network analyzer. Such processing means are not necessarily a vector network analyzer but can more generally be any other similar system for generating, receiving and analyzing electromagnetic waves to arrive at the same result.

It is specified that such a sample holder offers the advantage of being multifunctional and of being able to be used in very diverse and varied industrial fields of application of which the following may be cited particularly but not exclusively:
- field of application on solids: all solids of dielectric type (such as plastics) used in the construction of all products dedicated to the transmission and to the processing of information;
- fields of application on liquids:
  - a first field relates to the direct characterization of liquid or derivative materials such as gels, or viscous liquids (inert liquids and gels, biological liquids used for culture environment or living materials such as blood products);
  - a second field relates to indirect applications such as the detection and tracking of the presence of polluting products. This detection solution being able to be installed directly in-situ that is to say in pipelines or in flow bypasses. Another indirect application relates to biological or living products such as the tracking of the concentration of certain components of liquids such as blood derivatives;
- Another field of application relates to the characterization of materials of charged liquid, magnetic liquid, or else liquid crystal types. All such liquids are inert substances which have very mass-market applications and for which a knowledge of the electromagnetic characteristics is fundamental to the proper understanding of the interactions between these materials and the surrounding electronic circuits.

Numerous modifications can be made to the embodiment described above without departing from the scope of the invention.

Thus, the means of leaktight assembly and/or the means of clamping can differ, in the same manner as the means for centering the sample holder between the first and second connectors can differ. For example the sample holder can comprise cavities in which the ends of the first and second cores engage. It is also conceivable to have the screws distributed in a substantially homogeneous manner laterally to the second clamping means so that the screws pass through the thickness of said second clamping means and finish their paths in screw threads disposed laterally opposite on the exterior body.

Another possible alteration or modification could lie at the level of the third clamping means 31, it is possible to conceive of a lever or clip based latching based system which would make it possible to optimize the operations of opening and closing the support elements in order to change the sample holder.

Moreover it is also conceivable to add leaktightness means or means making it possible to package the material in a certain form and thus make it possible, for example, to package a sample of substance under determined pressure conditions. In this case the extra packaging means must make it possible to ensure a leaktightness of the cavity while withstanding a certain pressure.

Moreover, in the present case, the support device exhibits a coaxial electromagnetic wave guidance structure. However the sample holder described here can equally well be used with a circular or rectangular propagation structure. In the first case the sample holder is slightly modified by omitting the central core and the central drillings of the lateral partitions. In the second case the sample holder is modified by omitting the central core and the central drillings of the lateral partitions and by changing the shape of the right cross section, this right cross section then being rectangular, the lateral partitions then being slender parallelepipeds and the right cross section of the external body also being rectangular. Under these conditions the general shapes of the connectors must be adapted to suit the shape of the sample holder.

Moreover, the tubular guidance structure for the electromagnetic wave can also be of constant or variable dimension, for example cylindrical or conical for a waveguide of circular cross section or else truncated pyramidal for a waveguide of rectangular cross section.

Finally, the shoulders of the first and second connectors suitable for housing and positioning the sample holder can be of a different nature such that they are able mechanically to center the sample holder with respect to the support device.

The invention claimed is:

1. A sample holder for measurements of dielectric and/or magnetic characteristics of a sample, the sample holder system comprising:
    a central core having a first distal end extending outwardly with a reference axis (x) from the central core and a second opposing distal end extending outwardly with the reference axis from the central core;
    a first lateral wall having an outer edge and an orifice that engages the central core such that the first distal end of the central core extends through the orifice of the first lateral wall;
    a second lateral wall having an outer edge and an orifice that engages the central core such that the second distal end of the central core extends through the orifice of the second lateral wall;
    a tubular external body surrounding coaxially with the reference axis (x), the central core, the first lateral wall and the second lateral wall, the outer edge of the first lateral wall and the outer edge of the second lateral wall engaging the tubular external body such that the tubular external body, the central core, the first lateral wall, and the second lateral wall define a sample cavity;
    a first leaktight set linking, in a gas-tight and/or liquid-tight manner, the first lateral wall to the central core and to the external body;
    a second leaktight set linking, in a gas-tight and/or liquid-tight manner, the second lateral wall to the central core and to the external body;
    wherein laterally the external body exhibits recesses where the lateral walls are received and clamped by a first clamping means of each leaktight set.

2. The sample holder as claimed in claim 1, wherein the sample is made of pouring material, and wherein the sample holder comprises an entry and an exit of the sample allowing a flow of the pouring material in and out of the cavity.

3. The sample holder as claimed in claim 1, wherein the sample holder comprises means of measurement of intrinsic characteristics of the sample and/or means of varying these intrinsic characteristics in the sample holder.

4. The sample holder as claimed in claim 1, wherein the first lateral wall and the second lateral wall of the sample holder are made of dielectric material(s) and/or the central core and the external body are made of electrically conducting material(s).

5. The sample holder as claimed in claim 1, wherein the central core exhibits a central part and, laterally, a shaft extending along the reference axis (x) on either side of the central part, the lateral walls having a disk shape and being respectively received on the shaft, where they are clamped by a second clamping means of each leaktight set.

6. The sample holder as claimed in claim 5, wherein the second clamping means of each leaktight set comprise a second fastener operative to exert a compressive force between the central core and the corresponding lateral wall such that said lateral wall is substantially fixed to the central core.

7. The sample holder as claimed in claim 1, wherein the first distal end of the central core is operative to engage a first connector of a support device and the second distal end of the central core is operative to engage a second connector of said support device such that the support device supports the sample holder.

8. A sample holder for measurements of dielectric and/or magnetic characteristics of a sample, the sample holder system comprising:
    a central core having a first distal end extending outwardly with a reference axis (x) from the central core and a second opposing distal end extending outwardly with the reference axis from the central core;
    a first lateral wall having an outer edge and an orifice that engages the central core such that the first distal end of the central core extends through the orifice of the first lateral wall;
    a second lateral wall having an outer edge and an orifice that engages the central core such that the second distal end of the central core extends through the orifice of the second lateral wall;
    a tubular external body surrounding coaxially with the reference axis (x), the central core, the first lateral wall and the second lateral wall, the outer edge of the first lateral wall and the outer edge of the second lateral wall engaging the tubular external body such that the tubular external body, the central core, the first lateral wall, and the second lateral wall define a sample cavity;
    a first leaktight set linking, in a gas-tight and/or liquid-tight manner, the first lateral wall to the central core and to the external body;
    a second leaktight set linking, in a gas-tight and/or liquid-tight manner, the second lateral wall to the central core and to the external body;
    wherein laterally the external body exhibits recesses where the lateral walls are received and clamped by a first clamping means of each leaktight set;
    said first clamping means of each leaktight set comprising a first fastener operative to exert a compressive force between the corresponding lateral wall and the tubular external body.

9. The sample holder as claimed in claim 8, wherein the sample is made of pouring material, and wherein the sample holder comprises an entry and an exit of the sample allowing a flow of the pouring material in and out of the cavity.

10. The sample holder as claimed in claim 8, wherein the sample holder comprises means of measurement of intrinsic characteristics of the sample and/or means of varying these intrinsic characteristics in the sample holder.

11. The sample holder as claimed in claim 8, wherein the first lateral wall and the second lateral wall of the sample holder are made of dielectric material(s) and/or the central core and the external body are made of electrically conducting material(s).

12. The sample holder as claimed in claim 8, wherein the central core exhibits a central part and, laterally, a shaft extending along the reference axis (x) on either side of the central part, the lateral walls having a disk shape and being respectively received on the shaft, where they are clamped by a second clamping means of each leaktight set.

13. The sample holder as claimed in claim 12, wherein the second clamping means of each leaktight set comprise a second fastener operative to exert a compressive force between the central core and the corresponding lateral wall such that said lateral wall is substantially fixed to the central core.

14. The sample holder as claimed in claim 8, wherein the first distal end of the central core is operative to engage a first connector of a support device and the second distal end of the central core is operative to engage a second connector of said support device such that the support device supports the sample holder.

* * * * *